United States Patent
Aoki et al.

(10) Patent No.: US 9,242,947 B2
(45) Date of Patent: Jan. 26, 2016

(54) METHOD FOR PRODUCING SULFUR-CONTAINING EPOXY COMPOUND

(71) Applicant: MITSUBISHI GAS CHEMICAL COMPANY, INC., Tokyo (JP)

(72) Inventors: Takashi Aoki, Osaka (JP); Hiroshi Horikoshi, Chiba (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/374,352

(22) PCT Filed: Apr. 12, 2013

(86) PCT No.: PCT/JP2013/061017
§ 371 (c)(1),
(2) Date: Jul. 24, 2014

(87) PCT Pub. No.: WO2013/157490
PCT Pub. Date: Oct. 24, 2013

(65) Prior Publication Data
US 2014/0371475 A1   Dec. 18, 2014

(30) Foreign Application Priority Data

Apr. 16, 2012   (JP) ................... 2012-093196

(51) Int. Cl.
| | |
|---|---|
| C07D 301/24 | (2006.01) |
| C07D 301/02 | (2006.01) |
| C07D 301/26 | (2006.01) |
| C07D 303/34 | (2006.01) |

(52) U.S. Cl.
CPC ............ *C07D 301/02* (2013.01); *C07D 301/26* (2013.01); *C07D 303/34* (2013.01)

(58) Field of Classification Search
CPC ... C07D 301/26; C07D 301/02; C07D 303/34
USPC ...................................................... 549/520
See application file for complete search history.

(56) References Cited

U.S. PATENT DOCUMENTS

| | | | |
|---|---|---|---|
| 3,673,260 A | 6/1972 | Esclamadon et al. | |
| 5,807,975 A | 9/1998 | Amagai et al. | |
| 5,945,504 A | 8/1999 | Amagi et al. | |
| 2001/0002413 A1 | 5/2001 | Morijiri et al. | |
| 2013/0005993 A1* | 1/2013 | Kuad et al. | ........... 549/90 |

FOREIGN PATENT DOCUMENTS

| | | |
|---|---|---|
| CN | 103204831 A | 7/2013 |
| FR | 1 578 068 A | 8/1969 |
| FR | 1578068 | 8/1969 |
| JP | 09-71580 | 3/1997 |
| JP | 09-110979 | 4/1997 |
| JP | 09-255781 | 9/1997 |
| JP | 11-322930 | 11/1999 |
| JP | 2000-143651 | 5/2000 |
| JP | 2003-048883 | 2/2003 |
| JP | 2005-272418 | 10/2005 |
| JP | 2005272418 * | 10/2005 |
| JP | 2011-195487 | 10/2011 |

OTHER PUBLICATIONS

Search report from PCT/JP2013/061017, mail date is May 14, 2013.
European Search Report issued Jun. 12, 2015 in EP 13778911.1.
Fujisaki et al: "Synthesis of alkyl 3-chloro-2-hydroxopyropyl sulfides . . . ", Nippon Kagaku Kaisha, Jan. 1, 1975.
Chinese Office Action issued with respect to application No. 201380020112.7, mail date is Jun. 17, 2015.

* cited by examiner

*Primary Examiner* — T. Victor Oh
(74) *Attorney, Agent, or Firm* — Greenblum & Bernstein, P.L.C.

(57) ABSTRACT

An object of the present invention is to provide a method for producing a sulfur-containing epoxy compound producing no scum-like insoluble matter. According to the present invention, a sulfur-containing halohydrin compound is dripped into and reacted with a mixed solvent containing an organic solvent and a basic compound to provide the method for producing the sulfur-containing epoxy compound. According to aspects of the present invention, the organic solvent is at least one type of compound selected from toluene and benzene, the basic compound is at least one type of compound selected from sodium hydroxide, potassium hydroxide and calcium hydroxide, and the reaction temperature is between −5° C. and 30° C.

4 Claims, No Drawings

METHOD FOR PRODUCING SULFUR-CONTAINING EPOXY COMPOUND

TECHNICAL FIELD

The present invention relates to a sulfur-containing epoxy compound and a method for producing the same. The present invention particularly relates to a sulfur-containing epoxy compound, which may be a raw material of an episulfide compound suitably used for optical materials for a plastic lens, a prism, an optical fiber, an information recording substrate, a filter or the like, in particular for a plastic lens, and a method for producing the same.

BACKGROUND ART

Plastic materials are lightweight, highly tough and easy to be dyed, and therefore are widely used recently for various types of optical materials, particularly eyeglass lenses. Optical materials, particularly eyeglass lenses, are specifically required to have, as physical properties, low specific gravity, high transparency and low yellowness, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number is decreased. Therefore, it has been studied to improve both of the refractive index and the Abbe number. Among methods which have been proposed, the most representative method is a method using an episulfide compound as described in Patent Documents 1-3.

The episulfide compound is obtained by producing a sulfur-containing epoxy compound and then sulfidating the compound. As methods for producing a sulfur-containing epoxy compound, the production methods described in Patent Documents 4 and 5 have been proposed, and the yield and transparency of resin obtained by curing an episulfide compound obtained by sulfidation have been improved. Patent Document 6 also describes a method for producing a sulfur-containing epoxy compound.

PRIOR ART DOCUMENTS

Patent Documents

Patent Document 1: Japanese Laid-Open Patent Publication No. H09-71580
Patent Document 2: Japanese Laid-Open Patent Publication No. H09-110979
Patent Document 3: Japanese Laid-Open Patent Publication No. H09-255781
Patent Document 4: Japanese Laid-Open Patent Publication No. 2000-143651
Patent Document 5: Japanese Laid-Open Patent Publication No. 2003-48883
Patent Document 6: Japanese Laid-Open Patent Publication No. H11-322930

SUMMARY OF THE INVENTION

Problems to be Solved by the Invention

However, when using the aforementioned methods for producing a sulfur-containing epoxy compound, a scum-like insoluble matter may be generated at the time of extraction of the sulfur-containing epoxy compound, causing troubles such as a clogged pipe.

Therefore, the problem of the present invention is to provide a method for producing a sulfur-containing epoxy compound generating no scum-like insoluble matter.

Means for Solving the Problems

Under the above-described circumstances, the present inventors diligently made researches and found that a sulfur-containing epoxy compound can be produced without generating any scum-like insoluble matter by dripping a sulfur-containing halohydrin compound into a mixed solvent containing an organic solvent and an aqueous solution of a basic compound and reacting them. Specifically, the present invention is as follows:

1. A method for producing a sulfur-containing epoxy compound, which comprises dripping a sulfur-containing halohydrin compound into a mixed solvent containing an organic solvent and an aqueous solution of a basic compound; and reacting said sulfur-containing halohydrin compound with said mixed solvent.
2. The method for producing a sulfur-containing epoxy compound according to 1 above, wherein the sulfur-containing halohydrin compound is a compound represented by formula (1) below, and wherein the sulfur-containing epoxy compound is a sulfur-containing epoxy compound represented by formula (2) below:

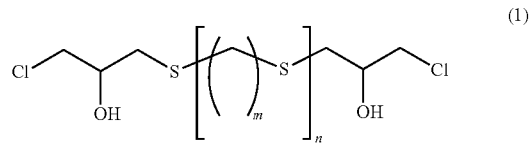

wherein m represents an integer from 0 to 4, n represents an integer from 0 to 2, with the proviso that when m is 0, n is not 2;

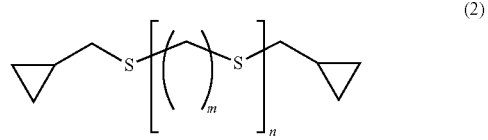

wherein m represents an integer from 0 to 4, n represents an integer from 0 to 2, with the proviso that when m is 0, n is not 2.

3. The method for producing a sulfur-containing epoxy compound according to 1 above, wherein the organic solvent is at least one type of compound selected from toluene and benzene.
4. The method for producing a sulfur-containing epoxy compound according to 1 above, wherein the basic compound is at least one type of compound selected from sodium hydroxide, potassium hydroxide and calcium hydroxide.
5. The method for producing a sulfur-containing epoxy compound according to 1 above, wherein the reaction temperature is between −5° C. and 30° C.

Advantageous Effects of the Invention

According to the production method of the present invention, it is possible to produce a sulfur-containing epoxy compound without generating any scum-like insoluble matter which is generated by the production method of prior art. Since no scum-like insoluble matter is generated by the production method of the present invention, it is possible to control troubles regarding the production such as a clogged pipe, and therefore it is very meaningful.

EMBODIMENTS FOR CARRYING OUT THE INVENTION

The present invention is characterized in that a sulfur-containing halohydrin compound is dripped into and reacted with a mixed solvent containing an organic solvent and an aqueous solution of a basic compound.

The sulfur-containing halohydrin compound to be used in the present invention includes all sulfur-containing halohydrin compounds, and specific examples thereof are classified into a compound having a chain aliphatic skeleton, a compound having an aliphatic cyclic skeleton and a compound having an aromatic skeleton and listed below.

Examples of the compound having a chain aliphatic skeleton include a compound represented by the following formula (1):

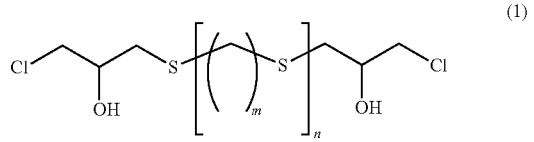

wherein m represents an integer from 0 to 4, n represents an integer from 0 to 2, with the proviso that when m is 0, n is not 2.

Examples of the compound having an aliphatic cyclic skeleton include a compound represented by the following formula (3) or (4):

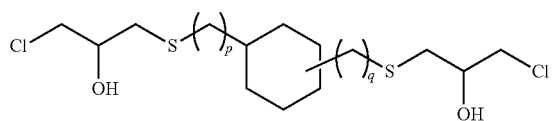

wherein p and q each independently represent an integer from 0 to 4;

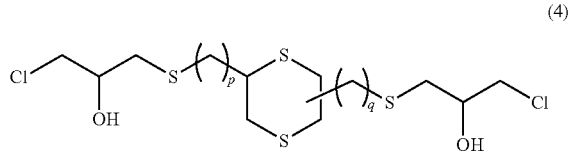

wherein p and q each independently represent an integer from 0 to 4.

Examples of the compound having an aromatic skeleton include a compound represented by the following formula (5):

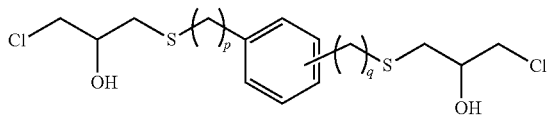

wherein p and q each independently represent an integer from 0 to 4.

Specific preferred examples of the above-described compounds include a compound having a chain aliphatic skeleton represented by formula (1) above, wherein n=0, n=1 and m=0 or 2, or n=2 and m=2, a compound having an aliphatic cyclic skeleton represented by formula (3) or (4) above, wherein p=q=0 or 1, and a compound having an aromatic cyclic skeleton represented by formula (5) above, wherein p=q=0 or 1.

Among them, the compound having a chain aliphatic skeleton represented by formula (1) is preferred, and specifically, bis(3-chloro-2-hydroxypropyl)sulfide (n=0 in formula (1)) and bis(3-chloro-2-hydroxypropyl)disulfide (n=1 and m=0 in formula (1)) are preferred. The most preferred compound is bis(3-chloro-2-hydroxypropyl)sulfide (n=0 in formula (1)).

Hereinafter, synthesis of the sulfur-containing halohydrin compound will be described.

The sulfur-containing halohydrin compound can be obtained by reacting epichlorohydrin with hydrogen sulfide or a polythiol compound. The polythiol compound includes all compounds by which the sulfur-containing epoxy compound can be obtained. For example, the compound represented by formula (1) can be made from hydrogen sulfide, methanedithiol, 1,2-dimercaptoethane, 1,3-dimercaptopropane, 1,4-dimercaptobutane, bis(2-mercaptoethyl)sulfide or the like, the compound represented by formula (3) can be made from 1,3-cyclohexanedithiol, 1,4-cyclohexanedithiol, 1,3-bis(mercaptomethyl)cyclohexane, 1,4-bis(mercaptomethyl)cyclohexane or the like, the compound represented by formula (4) can be made from 2,5-dimercapto-1,4-dithiane, 2,6-dimercapto-1,4-dithiane, 2,5-bis(mercaptomethyl)-1,4-dithiane, 2,6-bis(mercaptomethyl)-1,4-dithiane or the like, and the compound represented by formula (5) can be made from 1,3-benzenedithiol, 1,4-benzenedithiol, 1,3-bis(mercaptomethyl)benzene, 1,4-bis(mercaptomethyl)benzene or the like.

When reacting epichlorohydrin with hydrogen sulfide or the polythiol compound, a catalyst is preferably used. Examples of the catalyst include inorganic acids, organic acids, Lewis acids, silicic acid, boric acid, quaternary ammonium salts, inorganic bases and organic bases. Among them, organic acids, quaternary ammonium salts and inorganic bases are preferred, and quaternary ammonium salts and inorganic bases are more preferred. Specific examples thereof include tetramethylammonium chloride, tetramethylammonium bromide, tetramethylammonium acetate, tetraethylammonium chloride, tetraethylammonium bromide, tetraethylammonium acetate, tetrabutylammonium chloride, tetrabutylammonium bromide, tetrabutylammonium acetate, tetrahexylammonium chloride, tetrahexylammonium bromide, tetrahexylammonium acetate, tetraoctylammonium chloride, tetraoctylammonium bromide, tetraoctylammonium acetate, sodium hydroxide, potassium hydroxide, magnesium hydroxide and calcium hydroxide. Among them, sodium hydroxide, potassium hydroxide and calcium hydroxide are preferred.

The amount of the catalyst to be added is not particularly limited as long as it is for promoting a reaction, but is preferably 0.00001 to 0.5 mol, and more preferably 0.001 to 0.1 mol per 1 mol of epichlorohydrin. When the amount is less than 0.00001 mol, the reaction does not proceed or is too slow, and it is undesirable. When the amount is more than 0.5 mol, the reaction proceeds excessively and is difficult to be controlled, and it is undesirable.

The ratio between epichlorohydrin and hydrogen sulfide or the polythiol compound is not particularly limited as long as the reaction proceeds, but the molar ratio of epichlorohydrin to the thiol group (SH group) of the polythiol compound or H of hydrogen sulfide is preferably 0.3 to 4, more preferably 0.4 to 3, and even more preferably 0.5 to 2. When the molar ratio is less than 0.3 or more than 4, the amount of unreacted raw materials increases, and it is undesirable from the economical viewpoint.

The reaction temperature is not particularly limited as long as it is for promoting a reaction, but is preferably −10° C. to 100° C., more preferably 0° C. to 80° C., even more preferably 0° C. to 60° C., and most preferably 0° C. to 40° C. The reaction time is not particularly limited, but is usually 10 minutes to 20 hours. When the reaction temperature is lower than −10° C., the reaction does not proceed or is too slow, and it is undesirable. When the reaction temperature is higher than 100° C., oligomerization occurs, resulting in a high molecular weight, and it is undesirable.

A solvent may be used but does not have to be used. In the case of using the solvent, water, alcohols, ethers, ketones, aromatic hydrocarbons or halogenated hydrocarbons can be used. Specific examples thereof include water, methanol, ethanol, propanol, isopropanol, diethyl ether, tetrahydrofuran, dioxane, methyl cellosolve, ethyl cellosolve, butyl cellosolve, methyl ethyl ketone, acetone, benzene, toluene, xylene, dichloroethane, chloroform and chlorobenzene. Among them, water, methanol and toluene are preferred, and water and methanol are most preferred.

Further, the compound having a disulfide bond represented by formula (1), wherein m=0 and n=1, can be obtained by reacting epichlorohydrin with hydrogen sulfide to obtain a compound having a chloro group, an alcoholic hydroxyl group and a thiol group and then forming the disulfide bond by the coupling of two thiol groups by means of an intermolecular reaction using a halogen compound and a basic compound.

Specific examples of the halogen compound to be used for forming the disulfide bond include chlorine, bromine and iodine, and bromine and iodine are preferred. The halogen compound is used in an amount of 0.1 to 5 mol per 1 mol of the SH group. The amount is preferably 0.2 to 3 mol, and more preferably 0.3 to 1 mol. When the amount is less than 0.1 mol or more than 5 mol, the amount of unreacted raw materials increases, and it is undesirable from the economical viewpoint.

Specific examples of the basic compound include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Among them, sodium carbonate, potassium carbonate, magnesium carbonate, calcium carbonate, sodium hydrogen carbonate and potassium hydrogen carbonate are preferred.

The basic compound is used in an amount of 0.1 to 10 mol per 1 mol of the SH group. The amount is preferably 0.2 to 5 mol, and more preferably 0.3 to 3 mol. When the amount is less than 0.1 mol or more than 10 mol, the amount of unreacted raw materials increases, and it is undesirable from the economical viewpoint.

A solvent may be used but does not have to be used. In the case of using the solvent, water, alcohols, ethers, ketones, aromatic hydrocarbons or halogenated hydrocarbons can be used. Specific examples thereof include water, methanol, ethanol, propanol, isopropanol, diethyl ether, tetrahydrofuran, dioxane, methyl cellosolve, ethyl cellosolve, butyl cellosolve, methyl ethyl ketone, acetone, benzene, toluene, xylene, dichloroethane, chloroform and chlorobenzene. Among them, water, methanol and toluene are preferred, and water and methanol are most preferred.

The reaction temperature is not particularly limited as long as it is for promoting a reaction, but is preferably −10° C. to 80° C., more preferably 0° C. to 50° C., and even more preferably 0° C. to 40° C. The reaction time is not particularly limited, but is usually 20 hours or less. When the reaction temperature is lower than −10° C., the reaction does not proceed or is too slow, and it is undesirable. When the reaction temperature is higher than 80° C., oligomerization occurs, resulting in a high molecular weight, and it is undesirable.

The sulfur-containing halohydrin compound obtained in the above-described manner is dripped into and reacted with a mixed solvent containing an organic solvent and an aqueous solution of a basic compound to obtain a sulfur-containing epoxy compound.

The organic solvent to be used in the present invention is not particularly limited and any organic solvent may be used, but preferably alcohols, ethers, ketones, aliphatic hydrocarbons, aromatic hydrocarbons or halogenated hydrocarbons are used. These substances may be used solely or in combination. Specific examples of alcohols include methanol, ethanol, propanol and isopropanol. Specific examples of ethers include diethyl ether, tetrahydrofuran and dioxane. Specific examples of ketones include methyl cellosolve, ethyl cellosolve, butyl cellosolve, methyl ethyl ketone and acetone. Specific examples of aliphatic hydrocarbons include hexane, heptane and octane. Specific examples of aromatic hydrocarbons include benzene, toluene and xylene. Specific examples of halogenated hydrocarbons include dichloroethane, chloroform and chlorobenzene. Alcohols, aliphatic hydrocarbons and aromatic hydrocarbons are more preferably used, and specific examples thereof include methanol, propanol, isopropanol, hexane, heptane, benzene and toluene. Among them, alcohols and aromatic hydrocarbons are preferred, and specific examples thereof include methanol, propanol, isopropanol, benzene and toluene. Aromatic hydrocarbons are even more preferred, and specific examples thereof include benzene and toluene. Toluene is the most preferred substance.

The amount of the organic solvent is not particularly limited, but is usually 5 to 1000 parts by mass, preferably 50 to 500 parts by mass, and more preferably 100 to 300 parts by mass per 100 parts by mass of the sulfur-containing halohydrin compound.

The basic compound to be used in the present invention is not particularly limited and any basic compound may be used, but preferably an alkali metal or alkaline-earth metal salt is used. Specific preferred examples thereof include sodium carbonate, potassium carbonate, magnesium carbonate, calcium carbonate, sodium hydrogen carbonate, potassium hydrogen carbonate, sodium hydroxide, potassium hydroxide, magnesium hydroxide and calcium hydroxide. Among them, sodium hydroxide, potassium hydroxide, magnesium hydroxide and calcium hydroxide are preferably used, and sodium hydroxide and potassium hydroxide are more preferably used.

The basic compound is used in an amount of 0.5 to 10 equivalents per 1 equivalent of the sulfur-containing halohydrin compound. The amount is preferably 0.7 to 5 equivalents, and more preferably 0.8 to 2 equivalents. When the amount is less than 0.5 equivalent or more than 10 equivalent, the amount of unreacted raw materials increases, and it is undesirable from the economical viewpoint.

The above-described basic compound is used in the form of an aqueous solution. The amount of water is not particularly limited as long as the basic compound can be dissolved.

According to the present invention, the sulfur-containing halohydrin compound is dripped into and reacted with a mixed solvent containing an organic solvent and an aqueous solution of a basic compound. The method for dripping the sulfur-containing halohydrin compound is not particularly limited. The sulfur-containing halohydrin compound may be dripped directly, or may be dissolved in a solvent and then dripped, or may be dripped without isolation after synthesis of the sulfur-containing halohydrin compound. Preferably, a method in which the sulfur-containing halohydrin compound is dissolved in a solvent and then dripped, or a method in which the sulfur-containing halohydrin compound is dripped without isolation after synthesis of the sulfur-containing halohydrin compound are employed, and more preferably, a method in which the sulfur-containing halohydrin compound is dripped without isolation after synthesis of the sulfur-containing halohydrin compound is employed.

In the case where the sulfur-containing halohydrin compound is dissolved in a solvent and then dripped, the solvent to be used is not limited, but preferably water, alcohols, ethers, ketones, aliphatic hydrocarbons, aromatic hydrocarbons or halogenated hydrocarbons are used. These substances may be used solely or in combination. Specific examples of alcohols include methanol, ethanol, propanol and isopropanol. Specific examples of ethers include diethyl ether, tetrahydrofuran and dioxane. Specific examples of ketones include methyl cellosolve, ethyl cellosolve, butyl cellosolve, methyl ethyl ketone and acetone. Specific examples of aliphatic hydrocarbons include hexane, heptane and octane. Specific examples of aromatic hydrocarbons include benzene, toluene and xylene. Specific examples of halogenated hydrocarbons include dichloroethane, chloroform and chlorobenzene. Water and alcohols are more preferred, and specific examples thereof include water, methanol, propanol and isopropanol. Among them, water and methanol are particularly preferred. The amount of the solvent is not particularly limited, but is usually 5 to 1000 parts by mass, preferably 50 to 500 parts by mass, and more preferably 100 to 300 parts by mass per 100 parts by mass of the sulfur-containing halohydrin compound.

In the case where the sulfur-containing halohydrin compound is dripped without isolation after synthesis of the sulfur-containing halohydrin compound, a raw material, a solvent, a catalyst, etc. used at the time of synthesis of the sulfur-containing halohydrin compound may remain.

In the present invention, the reaction temperature, at which the sulfur-containing halohydrin compound is dripped into and reacted with a mixed solvent containing the organic solvent and an aqueous solution of the basic compound, is not particularly limited as long as it is for promoting the reaction, but is preferably −10° C. to 80° C., more preferably 0° C. to 50° C., and even more preferably 0° C. to 30° C. The reaction time is not particularly limited, but is usually 20 hours or less.

When the reaction temperature is lower than −10° C., the reaction does not proceed or is too slow, and it is undesirable. When the reaction temperature is higher than 80° C., oligomerization occurs, resulting in a high molecular weight, and it is undesirable.

After the reaction is completed, an organic layer may be separated directly, but it is also possible to add an organic solvent to perform extraction. According to the production method of the present invention, the generation of a scum-like insoluble matter is inhibited in this step to allow separation in the subsequent step of washing with water without any problem. The generation of scum causes poor interface separation, resulting in difficulty in the production, and in addition, the organic layer is lost, resulting in the reduction of yield.

The organic layer obtained is washed with water to remove the basic compound. After that, the organic solvent is distilled away, thereby obtaining the sulfur-containing epoxy compound.

Examples of the sulfur-containing epoxy compound obtained in the above-described manner include compounds described below.

Examples of compounds having a chain aliphatic skeleton include a compound represented by the following formula (2):

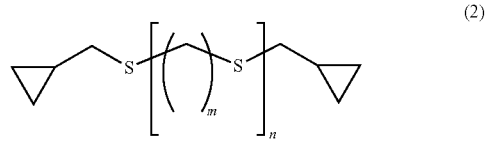

wherein m represents an integer from 0 to 4, n represents an integer from 0 to 2, with the proviso that when m is 0, n is not 2.

Examples of compounds having an aliphatic cyclic skeleton include a compound represented by the following formula (6) or (7):

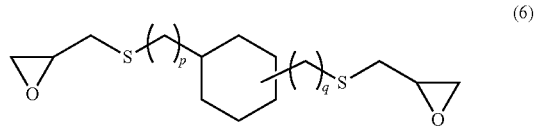

wherein p and q each independently represent an integer from 0 to 4;

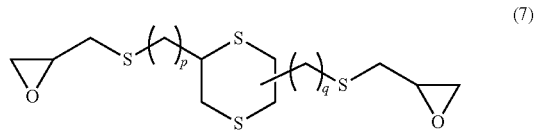

wherein p and q each independently represent an integer from 0 to 4.

Examples of compounds having an aromatic skeleton include a compound represented by the following formula (8):

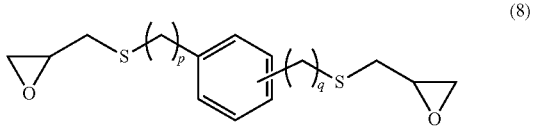

(8)

wherein p and q each independently represent an integer from 0 to 4.

Specific preferred examples of the above-described compounds include a compound having a chain aliphatic skeleton represented by formula (2) above, wherein n=0, n=1 and m=0 or 2, or n=2 and m=2, a compound having an aliphatic cyclic skeleton represented by formula (6) or (7) above, wherein p=q=0 or 1, and a compound having an aromatic cyclic skeleton represented by formula (8) above, wherein p=q=0 or 1.

Among them, the compound having a chain aliphatic skeleton represented by formula (2) is preferred, and specifically, bis(β-epoxypropyl)sulfide (n=0 in formula (2)) and bis(β-epoxypropyl)disulfide (n=1 and m=0 in formula (2)) are preferred. The most preferred compound is bis(β-epoxypropyl)sulfide (n=0 in formula (2)).

EXAMPLES

Hereinafter, the present invention will be specifically described by way of working examples, but the present invention is not limited thereto.

Example 1

185 g (2.0 mol) of epichlorohydrin, 10 ml of toluene and 0.97 g of tetra-n-butylammonium bromide were mixed together, and 35 g (1.0 mol) of hydrogen sulfide was blown into the mixture with stirring with the temperature of the solution being maintained at 20 to 25° C. After that, extraction was carried out using toluene to distil away the solvent, thereby obtaining 210 g (0.96 mol, yield: 96%) of bis(3-chloro-2-hydroxypropyl)sulfide (the compound represented by formula (1) above).

Next, bis(3-chloro-2-hydroxypropyl)sulfide described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 138 g (total yield: 95%) of bis(β-epoxypropyl)sulfide (the compound represented by formula (2) above).

Example 2

185 g (2.0 mol) of epichlorohydrin, 30 g of water, 5 g of methanol and 1.5 g of 32% aqueous solution of sodium hydroxide were mixed together, and 35 g (1.0 mol) of hydrogen sulfide was blown into the mixture with stirring with the temperature of the solution being maintained at 5 to 15° C., thereby obtaining 210 g (0.96 mol, yield: 96%) of bis(3-chloro-2-hydroxypropyl)sulfide.

Next, bis(3-chloro-2-hydroxypropyl)sulfide described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 138 g (total yield: 95%) of bis(β-epoxypropyl)sulfide.

Example 3

185 g (2.0 mol) of epichlorohydrin, 10 ml of toluene and 0.97 g of tetra-n-butylammonium bromide were mixed together, and 35 g (1.0 mol) of hydrogen sulfide was blown into the mixture with stirring with the temperature of the solution being maintained at 20 to 25° C., thereby obtaining bis(3-chloro-2-hydroxypropyl)sulfide.

Next, without isolation, bis(3-chloro-2-hydroxypropyl)sulfide described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 138 g (total yield: 95%) of bis(β-epoxypropyl)sulfide.

Example 4

185 g (2.0 mol) of epichlorohydrin, 30 g of water, 5 g of methanol and 1.5 g of 32% aqueous solution of sodium hydroxide were mixed together, and 35 g (1.0 mol) of hydrogen sulfide was blown into the mixture with stirring with the temperature of the solution being maintained at 5 to 15° C., thereby obtaining bis(3-chloro-2-hydroxypropyl)sulfide.

Next, without isolation, bis(3-chloro-2-hydroxypropyl)sulfide described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 138 g (total yield: 95%) of bis(β-epoxypropyl)sulfide.

Comparative Example 1

210 g (0.96 mol, yield: 96%) of bis(3-chloro-2-hydroxypropyl)sulfide was obtained by the technique of Example 1.

Next, bis(3-chloro-2-hydroxypropyl)sulfide described above was dripped into a reaction vessel containing 260 g of 32% aqueous solution of sodium hydroxide with the temperature of the solution in the reaction vessel being maintained at 0 to 10° C. Because the compound was dripped into the solution in which no organic solvent was present, a scum-like insoluble matter was generated at the point of the completion, and it was difficult to carry out separation.

Comparative Example 2

210 g (0.96 mol, yield: 96%) of bis(3-chloro-2-hydroxypropyl)sulfide was obtained by the technique of Example 1.

260 g of 32% aqueous solution of sodium hydroxide was dripped into a reaction vessel containing bis(3-chloro-2-hydroxypropyl)sulfide described above and 410 g of toluene with the temperature of the solution in the reaction vessel being maintained at 0 to 10° C. Because the aqueous solution of sodium hydroxide was dripped to carry out the synthesis, a scum-like insoluble matter was generated at the point of the completion, and it was difficult to carry out separation.

Comparative Example 3

Bis(3-chloro-2-hydroxypropyl)sulfide was obtained by the technique of Example 4. After that, without isolation, 260 g of 32% aqueous solution of sodium hydroxide was dripped into it with the temperature of the solution in a reaction vessel being maintained at 0 to 10° C. Because the aqueous solution of sodium hydroxide was dripped to carry out the synthesis, a scum-like insoluble matter was generated at the point of the completion, and it was difficult to carry out separation.

Comparative Example 4

Bis(3-chloro-2-hydroxypropyl)sulfide was obtained by the technique of Example 4. After that, without isolation, 410 g of toluene was added thereto, and 260 g of 32% aqueous solution of sodium hydroxide was dripped into it with the temperature of the solution in a reaction vessel being maintained at 0 to 10° C. Because the aqueous solution of sodium hydroxide was dripped to carry out the synthesis, a scum-like insoluble matter was generated at the point of the completion, and it was difficult to carry out separation.

Example 5

190 g (2.1 mol) of epichlorohydrin, 500 ml of methanol and 1.0 g of calcium hydroxide were mixed together, and 75 g (2.2 mol) of hydrogen sulfide was blown into the mixture with stirring with the temperature of the solution being maintained at 0 to 5° C., thereby obtaining chloromercaptopropanol. Next, 1000 ml of water and 168 g of sodium hydrogen carbonate were added thereto, and 254 g of iodine was added thereto with the temperature of the solution being maintained at 5 to 10° C. The mixture was reacted at 10° C. for 12 hours, and after that, it was subjected to filtration and drying, thereby obtaining bis(3-chloro-2-hydroxypropyl)disulfide.

Next, a mixed solution of bis(3-chloro-2-hydroxypropyl) disulfide described above and 250 g of methanol was dripped into a reaction vessel containing a mixed solvent consisting of 500 g of toluene and 240 g of 47% aqueous solution of sodium hydroxide with the temperature of the solution in the reaction vessel being maintained at 0 to 10° C. At the point of the completion, no scum-like insoluble matter was generated. 100 g of toluene was added to carry out extraction, the aqueous layer was removed, and the organic layer was washed with 180 g of water three times. After that, no scum-like insoluble matter was generated. After that, the solvent was distilled away, thereby obtaining 171 g of bis(β-epoxypropyl) disulfide.

Comparative Example 5

Bis(3-chloro-2-hydroxypropyl)disulfide was obtained by the technique of Example 5.

Next, 500 g of toluene and 240 g of 47% aqueous solution of sodium hydroxide were separately and simultaneously dripped into a reaction vessel containing bis(3-chloro-2-hydroxypropyl)disulfide described above and 250 g of methanol with the temperature of the solution in the reaction vessel being maintained at 0 to 10° C. Because toluene and the aqueous solution of sodium hydroxide were separately and simultaneously dripped to carry out the synthesis, a scum-like insoluble matter was generated at the point of the completion, and it was difficult to carry out separation.

Example 6

185 g (2.0 mol) of epichlorohydrin, 30 g of water, 30 g of methanol and 1.5 g of 32% aqueous solution of sodium hydroxide were mixed together, and 176 g (1.0 mol) of 1,3-bis(mercaptomethyl)cyclohexane was dripped into the mixture with stirring with the temperature of the solution being maintained at 5 to 15° C., thereby obtaining 1,3-bis(1-chloro-2-hydroxy-4-thiaheptyl)cyclohexane (the compound represented by formula (3) above).

Next, without isolation, 1,3-bis(1-chloro-2-hydroxy-4-thiaheptyl)cyclohexane described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 277 g (total yield: 96%) of 1,3-bis(β-epoxypropylthiomethyl)cyclohexane (the compound represented by formula (6) above).

Example 7

185 g (2.0 mol) of epichlorohydrin, 30 g of water, 30 g of methanol and 1.5 g of 32% aqueous solution of sodium hydroxide were mixed together, and 170 g (1.0 mol) of 1,3-bis(mercaptomethyl)benzene was dripped into the mixture with stirring with the temperature of the solution being maintained at 5 to 15° C., thereby obtaining 1,3-bis(1-chloro-2-hydroxy-4-thiaheptyl)benzene (the compound represented by formula (5) above).

Next, without isolation, 1,3-bis(1-chloro-2-hydroxy-4-thiaheptyl)benzene described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 274 g (total yield: 97%) of 1,3-bis(β-epoxypropylthiomethyl)benzene (the compound represented by formula (8) above).

Example 8

185 g (2.0 mol) of epichlorohydrin, 30 g of water, 30 g of methanol and 1.5 g of 32% aqueous solution of sodium hydroxide were mixed together, and 212 g (1.0 mol) of 2,5-bis(mercaptomethyl)-1,4-dithiane was dripped into the mixture with stirring with the temperature of the solution being maintained at 5 to 15° C., thereby obtaining 2,5-bis(1-chloro-2-hydroxy-4-thiaheptyl)-1,4-dithiane (the compound represented by formula (4) above).

Next, without isolation, 2,5-bis(1-chloro-2-hydroxy-4-thiaheptyl)-1,4-dithiane described above was dripped into a reaction vessel containing a mixed solvent consisting of 410 g of toluene and 260 g of 32% aqueous solution of sodium hydroxide with the temperature of the solution in the reaction vessel being maintained at 0 to 10° C. At the point of the completion, no scum-like insoluble matter was generated. The aqueous layer was removed, and the organic layer was washed with 180 g of water three times. After that, no scum-like insoluble matter was generated. After that, the solvent was distilled away, thereby obtaining 305 g (total yield: 94%) of 2,5-bis(β-epoxypropylthiomethyl)-1,4-dithiane (the compound represented by formula (7) above).

Comparative Example 6

1,3-bis(1-chloro-2-hydroxy-4-thiaheptyl)cyclohexane was obtained by the technique of Example 6. After that, without isolation, 410 g of toluene was added thereto, and 260 g of 32% aqueous solution of sodium hydroxide was dripped into it with the temperature of the solution in a reaction vessel being maintained at 0 to 10° C. Because the aqueous solution of sodium hydroxide was dripped to carry out the synthesis, a scum-like insoluble matter was generated at the point of the completion, and it was difficult to carry out separation.

Comparative Example 7

1,3-bis(1-chloro-2-hydroxy-4-thiaheptyl)benzene was obtained by the technique of Example 7. After that, without isolation, 410 g of toluene was added thereto, and 260 g of 32% aqueous solution of sodium hydroxide was dripped into it with the temperature of the solution in a reaction vessel being maintained at 0 to 10° C. Because the aqueous solution of sodium hydroxide was dripped to carry out the synthesis, a scum-like insoluble matter was generated at the point of the completion, and it was difficult to carry out separation.

Comparative Example 8

2,5-bis(1-chloro-2-hydroxy-4-thiaheptyl)-1,4-dithiane was obtained by the technique of Example 8. After that, without isolation, 410 g of toluene was added thereto, and 260 g of 32% aqueous solution of sodium hydroxide was dripped into it with the temperature of the solution in a reaction vessel being maintained at 0 to 10° C. Because the aqueous solution of sodium hydroxide was dripped to carry out the synthesis, a scum-like insoluble matter was generated at the point of the completion, and it was difficult to carry out separation.

The invention claimed is:

1. A method for producing a sulfur-containing epoxy compound, which comprises dripping a sulfur-containing halohydrin compound into a mixed solvent containing an organic solvent and an aqueous solution of a basic compound; and reacting said sulfur-containing halohydrin compound with said mixed solvent, (A) wherein the sulfur-containing halohydrin compound is a compound represented by formula (1) below, and wherein the sulfur-containing epoxy compound is a sulfur-containing epoxy compound represented by formula (2) below:

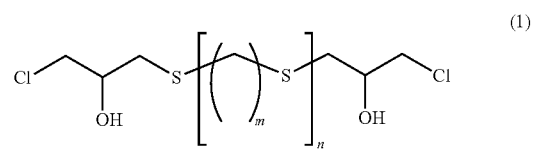

wherein m represents an integer from 0 to 4, n represents an integer from 0 to 2 with the proviso that when m is 0, n is not 2;

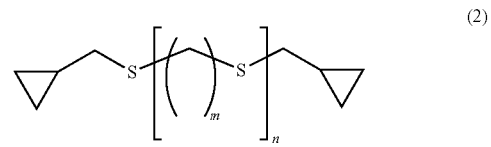

wherein m represents an integer from 0 to 4, n represents an integer from 0 to 2 with the proviso that when m is 0, n is not 2; or (B) wherein the sulfur-containing halohydrin compound is a compound represented by formula (3) below, and wherein the sulfur-containing epoxy compound is a sulfur-containing epoxy compound represented by formula (6) below:

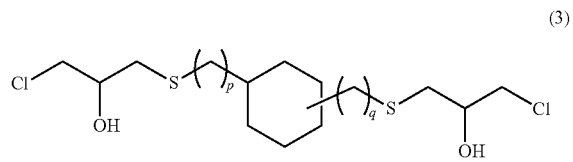

wherein p and q each independently represent an integer from 0 to 4;

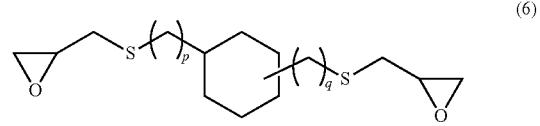

wherein p and q each independently represent an integer from 0 to 4; or (C) wherein the sulfur-containing halohydrin compound is a compound represented by formula (4) below, and wherein the sulfur-containing epoxy compound is a sulfur-containing epoxy compound represented by formula (7) below:

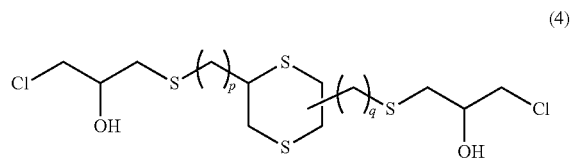

wherein p and q each independently represent an integer from 0 to 4;

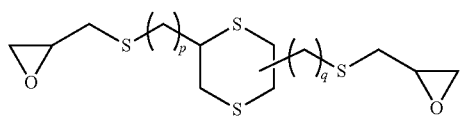
(7)

wherein p and q each independently represent an integer from 0 to 4; or (D) wherein the sulfur-containing halohydrin compound is a compound represented by formula (5) below, and wherein the sulfur-containing epoxy compound is a sulfur-containing epoxy compound represented by formula (8) below:

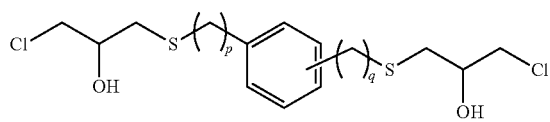
(5)

wherein p and q each independently represent an integer from 0 to 4;

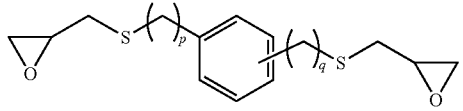
(8)

wherein p and q each independently represent an integer from 0 to 4.

2. The method for producing a sulfur-containing epoxy compound according to claim 1, wherein the organic solvent is at least one type of compound selected from toluene and benzene.

3. The method for producing a sulfur-containing epoxy compound according to claim 1, wherein the basic compound is at least one type of compound selected from sodium hydroxide, potassium hydroxide and calcium hydroxide.

4. The method for producing a sulfur-containing epoxy compound according to claim 1, wherein the reaction temperature is between −5° C. and 30° C.

* * * * *